United States Patent [19]

Cross

[11] 4,002,075
[45] Jan. 11, 1977

[54] LIQUID-MEASURING APPARATUS
[75] Inventor: David E. Cross, Folkestone, England
[73] Assignee: Smiths Industries Limited, London, England
[22] Filed: Aug. 15, 1975
[21] Appl. No.: 605,106

Related U.S. Application Data

[63] Continuation-in-part of Ser. No. 378,100, July 11, 1973, Pat. No. 3,888,126.

[30] Foreign Application Priority Data

Aug. 16, 1974 United Kingdom .............. 36164/74

[52] U.S. Cl. .................................. 73/426; 128/2 F
[51] Int. Cl.² ........................................ G01F 19/00
[58] Field of Search ............ 73/426, 222, 226, 194; 128/2 F, 295

[56] References Cited
UNITED STATES PATENTS 3,888,126  6/1975  Cross ................................. 73/426

FOREIGN PATENTS OR APPLICATIONS 1,184      1/1886  United Kingdom ................. 73/226
1,160,472  8/1969  United Kingdom ................. 73/226

*Primary Examiner*—Donald O. Woodiel
*Attorney, Agent, or Firm*—Pollock, VandeSande and Priddy

[57] ABSTRACT

Liquid-measuring apparatus for measuring the drainage of urine from a patient comprises a measuring cylinder and a bag which is of substantially larger capacity than the cylinder and is situated beneath the cylinder. Tubing extends downwardly to the bag from within a compartment of the cylinder, the compartment being formed by an additional tube which is closed at its upper end and perforated near its lower end. The cylinder is vented to ambient atmospheric pressure above the level of the upper end of the tubing connected to the bag. Every time urine collected in the cylinder reaches this level, an automatic siphon action drains a predetermined quantity of the urine from the cylinder, through the compartment and the tubing, into the bag. The total quantity of urine drained from the patient can be measured at any time by means of a coarse reading taken from the bag and a fine reading taken from the cylinder.

12 Claims, 4 Drawing Figures

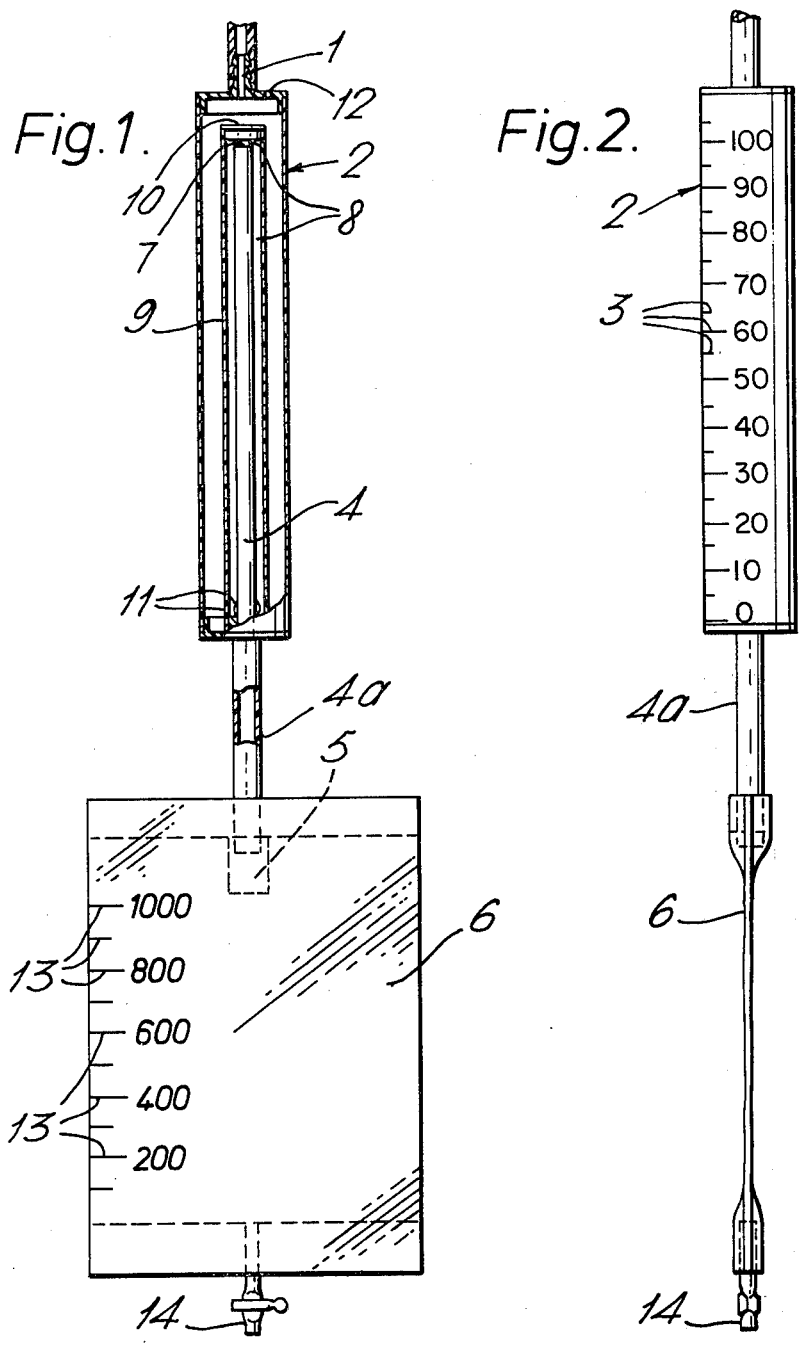

LIQUID-MEASURING APPARATUS

CROSS-REFERENCE TO RELATED APPLICATION

This application is a continuation-in-part application of my earlier U.S. patent application Ser. No. 378,100 filed July 11, 1973 (issued June 10, 1975 as U.S. Pat. No. 3,888,126).

BACKGROUND OF THE INVENTION

This invention relates to liquid-measuring apparatus.

This invention is concerned in particular, though not exclusively, with apparatus for providing a measure of the quantity of urine, or other body fluid, drained from a person under medical observation.

Measurement of the quantity, or rate, of drainage of urine from a patient is frequently necessary in the case of burn injury or following surgery. Conventionally, the measurement is made by feeding the urine via a catheter from the patient's bladder directly into a large-capacity container in the form of a bottle or bag. The accuracy with which such a container, a bag especially, can be calibrated and graduated to enable a direct reading of quantity to be made is limited by both practical and economic considerations. Accordingly it is usually the practice, where any sensible degree of accuracy is required, to drain the urine from the patient into a finely-graduated burette. Owing to the small capacity of the burette it is necessary to monitor its content closely and to empty it frequently. The burette is emptied, either through a tap at the bottom or by tipping it, whenever the urine reaches an upper measurement level, and the overall measurement is obtained by totalization of successive readings logged from the burette at these times. Concern with this procedure imposes a burden on the nurse or other medical attendant, and is wasteful of time. Furthermore the necessary logging and subsequent totalization of the readings is very much open to human error.

Liquid-measuring apparatus that may be used to avoid these disadvantages is disclosed in my earlier U.S. Pat. No. 3,888,126, issued June 10, 1975. With the particular form of apparatus described in that patent, a catheter from the patient's bladder feeds the urine directly into a first chamber which is provided in the form of a graduated measuring cylinder. An outlet at the bottom of the cylinder is connected by a tube to a non-return valve in the top of a transparent, flexible bag which forms a second, larger-capacity chamber of the apparatus. The tube, which provides a passageway intercoupling the two chambers, extends firstly upwardly from the outlet from the cylinder and then downwardly, around an inverted U-shaped bend, to the bag. There is no transfer of urine to the bag until it rises in the cylinder to the level of the inverted U-shaped bend, whereupon an automatic siphoning action comes into effect to drain the cylinder. The quantity transferred is the same every time and is, in the particular example described, a unit quantity of 100 c.c. The bag, which has a capacity much greater than that of the cylinder, is graduated in units of 100 c.c.

The successive steps of accumulating the urine in the cylinder and then transferring it automatically in the unit quantity to the bag proceeds as a continuous process, and the total quantity of urine drained from the patient, or the rate of such drainage, can be readily monitored, in units of 100 c.c., from the graduations of the bag. The cylinder is graduated in terms of 1 c.c. units so that an accurate measurement of the total quantity of urine involved can be derived from a 'fine' reading taken against the graduations of the cylinder, and a 'coarse' reading taken against the graduations of the bag.

The apparatus described in my earlier, above-mentioned patent has the advantage that it avoids the need for accurate calibration and fine graduation of a container capable of holding the full volume of liquid that is to be involved in the measurement. The calibration and graduation of the relevant container — the bag or second chamber — need only be to an accuracy that will enable discrimination of reading to be made between quantities that differ from one another by the transfer-quantity unit (e.g. 100 c.c.). Accuracy of measurement in this case is achieved by the transfer to the second chamber of liquid only in the unit quantity defined in relation to the smaller, and therefore more-readily calibrated, cylinder or first chamber. Furthermore, measurement to any fraction of the defined unit can be readily accommodated by providing appropriate graduation of this first chamber.

SUMMARY OF THE INVENTION

It is an object of the present invention to provide an improved form of apparatus described in my earlier U.S. Pat. No. 3,888,126 whereby manufacture of the apparatus is made simpler and more economical.

According to one aspect of this invention there is provided improved liquid-measuring apparatus wherein the upwardly-extending portion of the passageway intercoupling the two chambers comprises a compartment within the cylinder or first chamber, which compartment is open to the first chamber below, and closed to the first chamber above, the level to which liquid must rise in the first chamber before siphoning occurs. In addition, the downwardly-extending portion of the passageway comprises tubular means which opens at this level within the compartment.

The compartment may be defined by a tubular member located in the cylinder or first chamber. The wall of the tubular member is preferably perforated below the said level to open the compartment to the first chamber. In the circumstances in which the first chamber is cylindrical, it may be closed at one end by a cap, the tubular means and the tubular member being both carried by the cap with the tubular means extending through the cap.

The cylinder or first chamber may be a liquid-measuring device that is provided as a separate entity from the second chamber and is simply adapted to be coupled to a suitably-graduated larger-capacity chamber, such as the above-mentioned bag, to form the improved liquid-measuring apparatus of the present invention. In this respect, and according to another aspect of the invention, a liquid-measuring device has a graduated measuring chamber which is for receiving liquid to the level at which siphoning is to occur and which above this level is adapted to communicate with ambient atmospheric pressure. A compartment in the measuring chamber is open to the measuring chamber below this level and closed to the measuring chamber above this level. Tubular means opening at the said level extends downwardly from within the compartment so as thereby to provide the desired automatic siphon. The measuring chamber is graduated in terms of fractional parts of the unit quantity in which liquid is siphoned through the compartment and the tubular means.

The improved apparatus and device provided by the present invention are readily and economically manufactured. In particular, there is no requirement for specialised elbow or U-bend mouldings, which are difficult and expensive to produce, since the major parts of the apparatus or device can be made from standard tube stock.

BRIEF DESCRIPTION OF THE DRAWINGS

Liquid-measuring apparatus in accordance with this invention, and including a liquid-measuring device as referred to above, will now be described, by way of example, with reference to the accompanying drawings, in which:

FIG. 1 is a front view, partly in section, of the liquid-measuring apparatus;

FIG. 2 shows the apparatus in side view;

DESCRIPTION OF THE PREFERRED EMBODIMENTS

Figure 3:
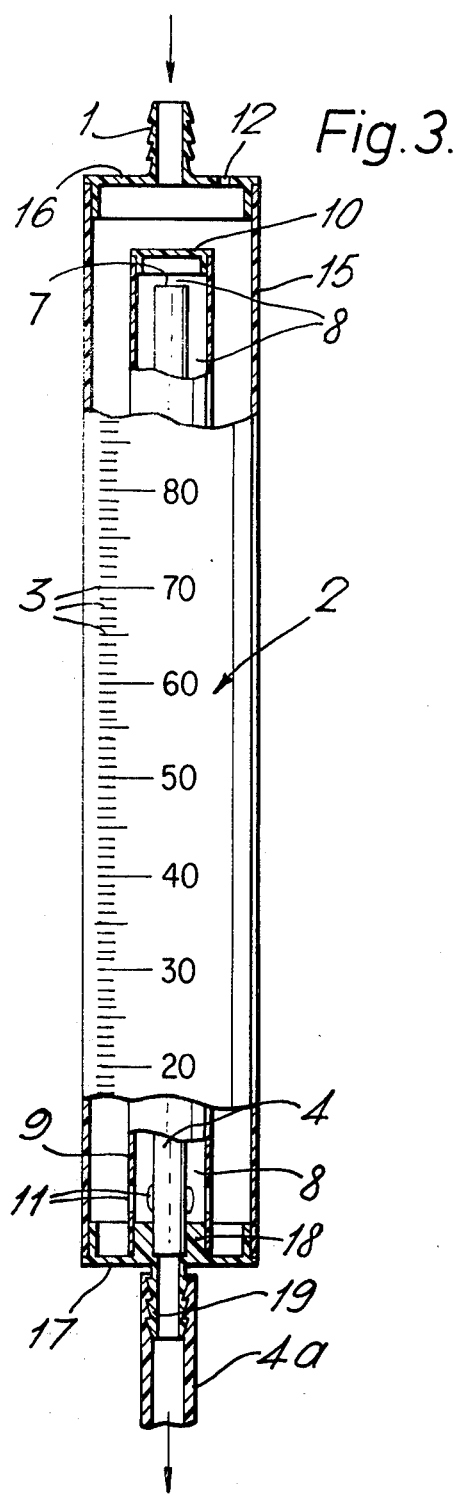
FIG. 3 shows, enlarged and in part-section, a measuring cylinder and associated tubes that form part of the apparatus of FIGS. 1 and 2, and constitute the liquid-measuring device as referred to above.

The apparatus shown in the drawings is for use in monitoring the quantity of urine draining through a catheter from the bladder of a hospital patient.

Referring to FIGS. 1 to 3, the apparatus receives the urine through an inlet 1 at the top of a substantially rigid and translucent measuring cylinder 2 that is calibrated from the bottom upwards in terms of cubic-centimeter graduations 3. The range of calibration extends a little (specifically 5 c.c., or thereabouts) beyond 100 c.c.

A tube 4 within the cylinder 2 is coupled at the bottom of the cylinder 2 to another tube 4a, and this tube 4a is connected at its lower end via a non-return valve 5 to a transparent, flexible bag 6 which has a liquid-holding capacity 10 (or some 15) times that of the cylinder 2. The upper end 7 of the tube 4 is located to open at a level slightly above that of the 100 c.c. graduation, within a compartment 8 of the cylinder 2 formed by a second tube 9 that surrounds the tube 4 coaxially. The compartment 8 is closed above the level of the open end 7 of the tube 4 by a cap 10 sealed to the upper end of the tube 9, but below that level is open to the cylinder 2 via a plurality of holes 11 in the tube 9 close to the bottom of the cylinder 2. The top of the cylinder 2 is vented to ambient atmosphere through an air-bleed opening 12 which is located above the level of the open end 7 of the tube 4.

As the cylinder 2 fills through the inlet 1, the urine rises up correspondingly in the compartment 8 between the tubes 4 and 9. When the level of urine in the cylinder 2 has risen above the 100 c.c. graduation, there is overflow into the open end 7 of the tube 4 such that with the bag 6 appropriately located below the holes 11, an automatic siphoning action takes place. By this action substantially all the content of the cylinder 2 is transferred through the holes 11, up the compartment 8, down the tubes 4 and 4a and through the non-return valve 5 into the bag 6. Transfer ceases when the urine in the cylinder 2 falls to the level of the holes 11, by which time exactly 100 c.c. has been siphoned over.

The diameters of the tubes 4 and 9 are chosen such that the width of the annular part of the compartment 8 between them is sufficient to ensure that any air bubbles forming at the end of the transfer collapse before reaching the open end 7 of the tube 4 and are therefore not transferred to the bag 6. The width of the annular part of the compartment 8 is also sufficient to provide that the column of urine (nominally 5 c.c. in volume) remaining in the compartment 8 at the end of the transfer collapses as soon as air is drawn through the holes 11 from the cylinder 2. Thus the urine collects in the bottom of the tube 9 and in the region of the holes 11 at the bottom of the cylinder 2, instead of being held in the compartment 8 by capillary action. This breaks the siphoning action positively, and avoids creation of an air lock.

As drainage from the patient continues, there is again accumulation of urine in the cylinder 2 until the level reaches the open end 7 of the tube 4, whereupon automatic siphoning takes place to empty the cylinder 2 almost completely by transfer of a second unit quantity of 100 c.c. of urine into the bag 6. The successive steps of urine accumulation, and automatic transfer to the bag 6 of a unit quantity of 100 c.c., then repeat again and again as a continuous process throughout the period of drainage. At any time the total quantity that has been transferred is indicated in units of 100 c.c. against graduations 13 in these terms on the wall of the transparent bag 6. This reading, taken with the 'fine' reading of the quantity then collected in the cylinder 2, provides accurate measurement of the drainage from the patient.

The readings, which may be taken quickly and surely without any disagreeable exposure to the urine, are to an accuracy not readily possible, for practical or economic reasons, with the bag 6 or any other large-capacity container by itself. The graduations 13 of the bag 6 need not in fact be provided to any higher degree of accuracy than is sufficient to enable discrimination to be made with certainty between successive unit quantities of 100 c.c. The fine accuracy of the measurement lies in the calibration of the cylinder 2 and the constancy of the automatic transfer process therefrom.

Although the opening 12 for venting the interior of the cylinder 2 to ambient atmospheric pressure is shown open in FIGS. 1 and 3, it is preferable in practice to provide a bacterial filter, for example a cotton-wool plug, in this opening so as to maintain sterility and also avoid the danger of ascending infection from the urine to the bladder.

Figure 4:
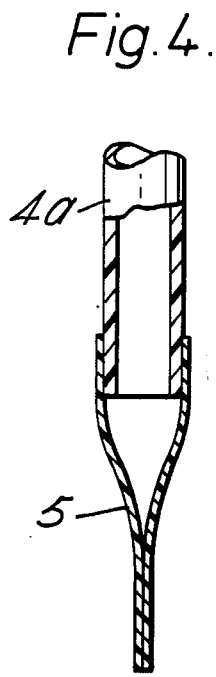
FIG. 4 illustrates the construction of a non-return valve of the apparatus.

The non-return valve 5, which, as illustrated in FIG. 4, may consist of a very thin-walled tube that closes in upon itself under anything but internally-applied liquid-pressure, serves to prevent reflux or spillage of urine from the bag 6. A tap or, as shown, a releasably-clamped outlet tube 14, at the bottom of the bag 6, enables the collected urine to be run off when desired.

The tube 4a may be uncoupled from the tube 4, so that the cylinder 2 and its tubes 4 and 9 provide a device for liquid measurement as a separate unitary structure. Such a structure may be coupled up to a standard urine-collection bag or to any other suitable (and not necessarily flexible) large-capacity container, for measuring purposes.

The apparatus of this invention has the advantage that it may be readily manufactured without, for example, purpose-made elbow and U-bend mouldings. Thus, with reference in particular to FIG. 3, the cylinder 2 is formed from an extruded plastics tube 15 and upper and lower plastics end-caps 16 and 17. The inlet 1 is an integral part of the upper end-cap 16, which also has a hole formed therein to provide the opening 12. The lower end-cap 17 has an inwardly-directed annular flange 18 axially aligned with an outlet 19 to which the tube 4a is to be attached.

Both the inlet 1 and the outlet 19 are circumferentially ribbed for retaining tubes pushed over them. The tube 4 is sealed to the inner wall of the flange 18, and the tube 9, closed by its cap 10 and punched with the holes 11, is sealed to the outer wall of the flange 18 in the inverted position over the open end 7 of the tube 4. The lower ends of the tubes 4 and 9 abut the inner face of the lower end-cap 17, thus accurately determining the positioning of those ends. Consequently, the volume of the unit quantity of urine to be transferred during each siphon action is conveniently controlled by the length of the tube 4.

The component parts of the assembly may be sealed together by adhesive or by welding, and the graduations 3 of the cylinder 2 may be provided by a pre-printed adhesive tape fixed to the outer surface of the tube 15.

The annular radius of the compartment 8, that is to say the distance between the outer surface of the tube 4 and the inner surface of the tube 9, is preferably chosen to be equal to the inner radius of the tube 4, in order to provide for maximum rate of flow during siphoning. To this end, the ratio of the inner radii of the tubes 4 and 9 should be approximately 1:2, although the exact value will depend on the wall-thickness of the tube 4.

Although in the example given above, the transfer-quantity unit is 100 c.c., it may clearly be arranged to be smaller or larger than this by suitable choice of the dimensioning of the cylinder 2 and the height of the open end 7 of the tube 4 above the holes 11. A smaller quantity unit might well be preferable where, for example, the apparatus is for use in blood-, rather than urine-, measurement.

I Claim:

1. In liquid-measuring apparatus which comprises a first chamber having an inlet for supplying the liquid to be measured to a predetermined level in said first chamber, said first chamber communicating with ambient atmospheric pressure above said predetermined level, a second chamber for the liquid being measured, said second chamber having a substantially larger liquid-holding capacity than said first chamber, and a passageway intercoupling the two chambers for automatically conveying selected increments of the liquid being measured from the first chamber to the second chamber, said passageway opening into said first chamber below said predetermined level and including a first portion extending upwardly to said predetermined level and a second portion extending downwardly from the said predetermined level to said second chamber so as thereby to provide an automatic siphon for draining a predetermined unit quantity of the liquid out of the said first chamber and into said second chamber in response to the liquid content of the said first chamber reaching said predetermined level: the improvement wherein the said upwardly-extending first portion of said passageway comprises a compartment within said first chamber, said compartment being open to said first chamber below said predetermined level and being closed to said first chamber above said predetermined level, and wherein the said downwardly-extending second portion of said passageway comprises tubular means which opens at said predetermined level within said compartment of said first chamber.

2. Apparatus according to claim 1, wherein said compartment is defined by a tubular member disposed in said first chamber.

3. Apparatus according to claim 2, wherein the wall of said tubular member is perforated below said predetermined level.

4. Apparatus according to claim 2, wherein said first chamber is cylindrical and is closed by a cap at one end thereof, said tubular means and said tubular member being both carried by said cap, and said tubular means extending through said cap.

5. Apparatus according to claim 1, wherein said second chamber is a bag.

6. Apparatus according to claim 1, including a non-return valve coupled to said tubular means for inhibiting passage of liquid up said tubular means from said second chamber.

7. Apparatus according to claim 1, wherein said second chamber is graduated in terms of the said unit quantity of liquid.

8. Apparatus according to claim 1, wherein said first chamber is graduated in terms of fractional parts of the said unit quantity of liquid.

9. A medico-surgical drainage-measuring device for measurement of liquid drained from patient, comprising a graduated measuring chamber which is for receiving said liquid to a predetermined level and which above this level is adapted to communicate with ambient atmospheric pressure, a compartment within said measuring chamber, said compartment being open to said measuring chamber below, and closed above, said predetermined level, and tubular means opening at said predetermined level and extending downwardly from said compartment so as thereby to provide an automatic siphon for passing a predetermined unit quantity of the liquid out of said measuring chamber via said compartment and said tubular means whenever the liquid content of said measuring chamber reaches said predetermined level, said tubular means including a non-return valve to inhibit reflux of said liquid up said tubular means, and said measuring chamber being graduated in terms of fractional parts of the said unit quantity.

10. Urine-measuring apparatus comprising a graduated measuring chamber which is for receiving urine to a predetermined level and which above this level is vented to ambient atmospheric pressure, a urine-collection bag having a substantially larger urine-holding capacity than said measuring chamber, a tubular member within said measuring chamber, said tubular member being open to said measuring chamber below, and closed above, said predetermined level, and tubular means opening at said predetermined level within said tubular member and extending downwardly into said bag, whereby said tubular member and said tubular means provide an automatic siphon for passing a predetermined unit quantity of urine out of said measuring chamber into said bag whenever the urine content of the said measuring chamber reaches said predetermined level.

11. Apparatus according to claim 10 wherein said measuring chamber is graduated in terms of fractional parts of the said unit quantity of urine.

12. Apparatus according to claim 11, wherein said bag is graduated in terms of said unit urine-quantity.

* * * * *